(12) United States Patent
Kuyava (10) Patent No.: US 7,250,026 B2
(45) Date of Patent: Jul. 31, 2007

(54) IMPLANTABLE PENILE PROSTHESIS PUMP

(75) Inventor: Charles C. Kuyava, Eden Prairie, MN (US)

(73) Assignee: AMS Research Corporation, Minnetonka, MN (US)

( * ) Notice: Subject to any disclaimer, the term of this patent is extended or adjusted under 35 U.S.C. 154(b) by 266 days.

(21) Appl. No.: 10/957,189

(22) Filed: Oct. 1, 2004

(65) Prior Publication Data

US 2005/0113638 A1    May 26, 2005

Related U.S. Application Data

(60) Provisional application No. 60/508,123, filed on Oct. 2, 2003.

(51) Int. Cl.
*A61F 5/00* (2006.01)
(52) U.S. Cl. .................................................. 600/40
(58) Field of Classification Search ............ 600/38–41, 600/29–32; 623/11.11; 128/843
See application file for complete search history.

(56) References Cited

U.S. PATENT DOCUMENTS

| 3,954,102 | A | 5/1976 | Buuck |
| 4,222,377 | A | 9/1980 | Burton |
| 4,224,934 | A | 9/1980 | Scott et al. |
| 4,235,227 | A | 11/1980 | Yamanaka |
| 4,267,829 | A | 5/1981 | Burton et al. |
| 4,383,525 | A | 5/1983 | Scott et al. |
| 4,407,278 | A | 10/1983 | Burton et al. |
| 4,412,530 | A | 11/1983 | Burton |
| 4,441,491 | A | 4/1984 | Evans, Sr. |
| 4,566,446 | A | 1/1986 | Fogarty |
| 4,572,168 | A | 2/1986 | Fischell |
| 4,590,927 | A | 5/1986 | Porter et al. |
| 4,596,242 | A | 6/1986 | Fischell |
| 4,602,625 | A | 7/1986 | Yachia et al. |
| 4,651,721 | A | 3/1987 | Mikulich et al. |
| 4,653,485 | A | 3/1987 | Fischell |
| 4,682,583 | A | 7/1987 | Burton et al. |

(Continued)

FOREIGN PATENT DOCUMENTS

DE    25 37 506 A1    3/1977

(Continued)

OTHER PUBLICATIONS

Gregory, John G. et al., The Inflatable Penile Prosthesis: Failure of the Rear Tip Extender in Reducing the Incidence of Cylinder Leakage, The Journal of Urology, vol. 131, pp. 668-669 (Apr. 1984).

(Continued)

*Primary Examiner*—John P. Lacyk
(74) *Attorney, Agent, or Firm*—Jose' W. Jimenez; Kimberly K. Baxter (57) ABSTRACT

A penile prosthesis is provided, which includes at least one cylinder, a reservoir, and a pump including a pump housing, at least one reservoir channel fluidly coupling the pump housing to the reservoir, at least one cylinder tube fluidly connecting the pump housing to the cylinders, and a fluid passageway fluidly coupled to the cylinder tube and a transfer chamber. The pump also includes a pump bulb fluidly connected to the fluid passageway between the bypass input channel and bypass output channel along the length of the fluid passageway.

9 Claims, 7 Drawing Sheets

U.S. PATENT DOCUMENTS

| | | | |
|---|---|---|---|
| 4,718,410 A | 1/1988 | Hakky |
| 4,782,826 A | 11/1988 | Fogarty |
| 4,807,608 A | 2/1989 | Levius |
| 4,895,139 A | 1/1990 | Hauschild et al. |
| 5,010,882 A | 4/1991 | Polyak et al. |
| 5,048,510 A | 9/1991 | Hauschild et al. |
| 5,062,417 A | 11/1991 | Cowen |
| 5,112,295 A | 5/1992 | Zinner et al. |
| 5,114,398 A | 5/1992 | Trick et al. |
| 5,141,509 A | 8/1992 | Burton et al. |
| 5,167,611 A | 12/1992 | Cowan |
| 5,171,272 A | 12/1992 | Levius |
| 5,250,020 A | 10/1993 | Bley |
| 5,263,981 A | 11/1993 | Polyak et al. |
| 5,344,388 A | 9/1994 | Maxwell et al. |
| 5,704,895 A | 1/1998 | Scott et al. |
| 5,851,176 A | 12/1998 | Willard |
| 6,171,233 B1 | 1/2001 | Willard |
| 6,443,887 B1 | 9/2002 | Derus et al. |
| 6,533,719 B2 | 3/2003 | Kuyava et al. |
| 6,558,315 B1 | 5/2003 | Kuyava |
| 6,723,042 B2 | 4/2004 | Almli et al. |
| 6,730,017 B2 | 5/2004 | Henkel et al. |
| 2002/0033564 A1 | 3/2002 | Koyfman |
| 2002/0082709 A1 | 6/2002 | Almli et al. |
| 2002/0091302 A1 | 7/2002 | Kuyava et al. |
| 2003/0028076 A1 | 2/2003 | Kuyava et al. |

FOREIGN PATENT DOCUMENTS

| | | |
|---|---|---|
| EP | 0 397 500 A2 | 11/1990 |
| WO | WO 92/03107 A | 3/1992 |

OTHER PUBLICATIONS

Hellstrom, WJG, Three-Piece Inflatable Penile Prosthesis Components (Surgical Pearls on Reservoirs, Pumps, and Rear-Tip Extenders), Int'l J of Impotence Research, vol. 15, Suppl. 5, pp. S136-138 (2003).

Joseph, David et al., Bilateral Dislocation of Rear Tip Extenders From the Inflatable Penile Prosthesis, The Journal of Urology, vol. 128, pp. 1317-1318 (Dec. 1982).

Kim, Sae-Chul, M.D., Mechanical Reliability of AMS Hydraulic Penile Prostheses, Journal of Korean Medical Science, vol. 10, No. 6, pp. 422-425 (Dec. 1995).

Levine, Laurence A. et al., Mechanical Reliability and Safety of, and Patient Satisfication with the Ambicor Inflatable Penile Prosthesis: Results of a 2 Center Study, The Journal of Urology, vol. 166, pp. 932-937 (Sep. 2001).

Malloy, Terrance R. et al., Improved Mechanical Survival with Revised Model Inflatable Penile Prosthesis Using Rear-Tip Extenders, The Journal of Urology, vol. 128, pp. 489-491 (Sep. 1982).

Montague, Drogo K., Experience with Semirigid Rod and Inflatable Penile Prosthesis, The Journal of Urology, vol. 129, pp. 967-968 (May 1983).

Mooreville, Michael et al., Implantation of Inflatable Penile Prosthesis in Patients with Severe Corporeal Fibrosis: Introduction of a New Penile Cavernotome, The Journal of Urology, vol. 162, pp. 2054-2057 (Dec. 1999).

Mulcahy, John J., Distal Corporoplasty for Lateral Extrusion of Penile Cylinders, The Journal of Urology, vol. 161, pp. 193-195 (Jan. 1999).

Parulkar, B.G. et al., Revision Surgery for Penile Implants, Int. J. Impotence Res., vol. 6, pp. 17-23 (1994).

Randrup, Eduardo R., M.D., Penile Implant Surgery: Rear Tip Extender That Stays Behind, Urology, vol. XXXIX, No. 1, pp. 667-669 (Jan. 1992).

Stein, Avi et al., Malleable Penile Prosthesis Removal Leaving Behind the Rear Tip Extenders; A Clinical Presentation, Urol. Int., 50, pp. 119-120 (1993).

AMS700™ *Inflatable Penile Prosthesis Product Line, Inservice Script* brochure, American Medical Systems (1992).

*Ultrex/Ultrex Plus* brochure, American Medical Systems, Inc. (1998).

Description of Ultrex Fabric and Yarns (Mar. 30, 2001).

Mentor Alpha I® Inflatable Penile Prosthesis, Surgical Protocol, 15 pages (1998).

Mentor Urology Products, 20 pages (May 1998).

Mentor Alpha I®, The Results are In, 14 pages (Apr. 1997).

Mentor Alpha I® Narrow Base, Simplifying Penile Implant Surgery by Making Difficult Cases More Manageable, 2 pages (Oct. 1996).

Mentor® Acu-Form® Penile Prosthesis, 2 pages (Aug. 1997).

Mentor® Acu-Form® Penile Prosthesis, Malleable Penile Prosthesis, Surgical Protocol, 8 pages (Sep. 1997).

Mulcahy, John J., Another Look at the Role of Penile Prosthesis in the Management of Impotence, pp. 169-185 (1997).

IMPLANTABLE PENILE PROSTHESIS PUMP

REFERENCE TO RELATED APPLICATION

This application claims the benefit of U.S. Provisional application having Ser. No. 60/508,123, filed Oct. 2, 2003, entitled "IMPLANTABLE PENILE PROSTHESIS HAVING A PRESSURIZED RESERVOIR," which application is incorporated herein by reference in its entirety.

TECHNICAL FIELD

The present invention relates to systems for treating erectile dysfunction and other urological disorders. In particular, the invention relates to inflatable implantable penile prostheses.

BACKGROUND OF THE INVENTION

One common treatment for male erectile dysfunction includes the implantation of a penile implant device. One type of penile implant device includes a pair of cylindrical prostheses that are implanted into the corpus cavernosae of the penis. Typically, the cylindrical prostheses or cylinders are inflatable and are connected to a fluid-filled reservoir through a pump and valve assembly. With one such type of system, one tube extends from each of the two cylindrical prostheses and connects to the pump, and one tube connects the pump to the reservoir. The pump is typically surgically implanted into the scrotum of the patient and the reservoir is implanted in the abdomen, with the tubes fluidly connecting the components. To activate the penile implant device, the patient actuates the pump using one of a variety of methods that cause fluid to be transferred from the reservoir through the pump and into the cylindrical prostheses. This results in the inflation of the prostheses and produces rigidity for a normal erection. Then, when the patient desires to deflate the prostheses, a valve assembly within the pump is actuated in a manner such that the fluid in the prostheses is released back into the reservoir. This deflation returns the penis to a flaccid state.

In three-piece systems such as those described above, the reservoir can sometimes be unintentionally compressed by bending or other pressure in the abdomen, which can lead to an inadvertent and undesirable spontaneous inflation of the cylinders. This can occur because many pump designs are not intended to prevent movement of fluid from the reservoir to the cylinders when the pump is subjected to pressurized fluid from a compressed reservoir. For one example, a pump that includes various poppets, springs, and valve seats can provide for fluid-tight seals for prevention of certain fluid movement under normal reservoir pressures. However, these same fluid-tight seals may be broken or opened when subjected to increased external pressure from the reservoir, thereby allowing fluid to move to and inflate the cylinders. This cylinder inflation can be embarrassing and uncomfortable for the user.

With many penile implant devices or systems, due to the positioning of the pieces of each system relative to each other and the type of pumping mechanism provided with the system, some systems require relatively significant manipulation by the user to transfer fluid to and from the cylindrical prostheses. Such manipulation may be either time-consuming or difficult, particularly for users who have problems with dexterity or complicated instructions. Thus, it is desirable to provide an inflatable prosthetic penile device or system that is easy to activate for cylinder inflation and deflation, and that minimizes or eliminates the chances of spontaneous cylinder inflation.

BRIEF DESCRIPTION OF THE DRAWINGS

The present invention will be further explained with reference to the appended Figures, wherein like structure is referred to by like numerals throughout the several views, and wherein.

DETAILED DESCRIPTION OF THE PREFERRED EMBODIMENTS

Figure 1:
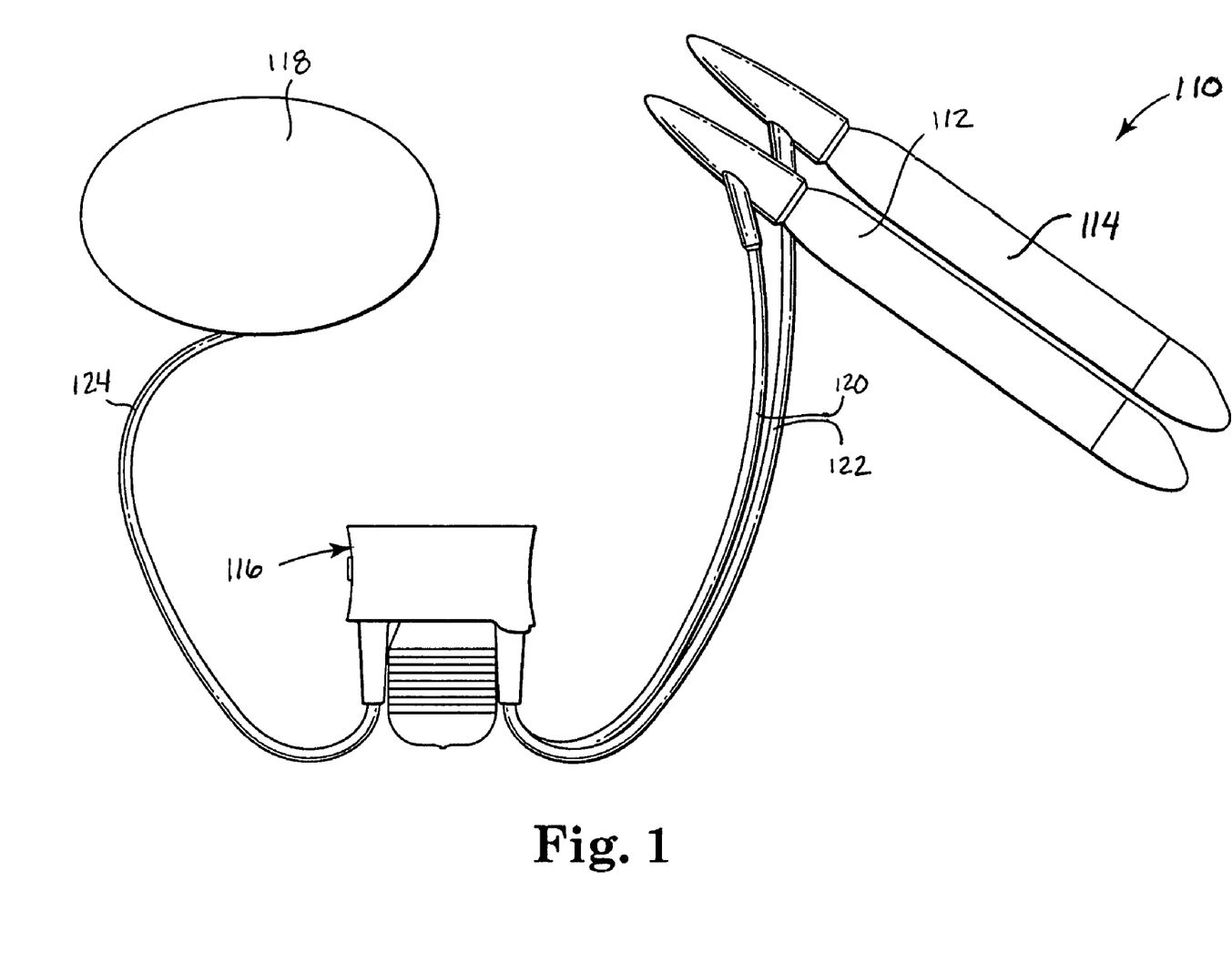
FIG. 1 is a top view of a three-piece implantable penile prosthesis device including a pair of penile prostheses, a pump, and a reservoir.

Referring now to the Figures, wherein the components are labeled with like numerals throughout the several Figures and initially to FIG. 1, one preferred configuration of a surgically implantable penile prosthesis device 110 having a three-piece design is illustrated. As shown, the device 110 generally includes first and second inflatable penile cylinders 112 and 114, respectively, a pump 116, and a reservoir 118. The first penile cylinder 112 is fluidly coupled to the pump 116 by a tube 120 and the second penile cylinder 114 is fluidly coupled to the pump 116 by a tube 122. The pump 116 is fluidly coupled to the reservoir 118 by a tube 124. The cylinders 112 and 114 designed for surgical implantation into the corpus cavernosa regions of a penis, the pump 116 is implantable within the scrotum of a patient, and the reservoir 118 is designed for implantation within the abdomen of the patient. In use, the patient can activate the pump 116 in some manner (e.g., squeezing the pump 116 in a particular way to open a valve) to move fluid from the reservoir 118 to inflate the penile cylinders 112 and 114 and provide an erection. Similarly, the patient can activate the pump 116 to return fluid to the reservoir 118 and thereby deflate the penile cylinders 112 and 114 and return the cylinders to a flaccid condition. A wide variety of configurations of penile prosthesis devices may be included within the scope of the invention, however, where the device 110 of FIG. 1 is intended to illustrate one representative system configured in accordance with the invention. For example, a number of different types of pump configurations may be used, such as those that require very little manipulation to move fluid between the reservoir and cylinders, or those that instead require the user to repeatedly squeeze the pump body for fluid transfer within the penile prosthesis device or system.

Figure 2:
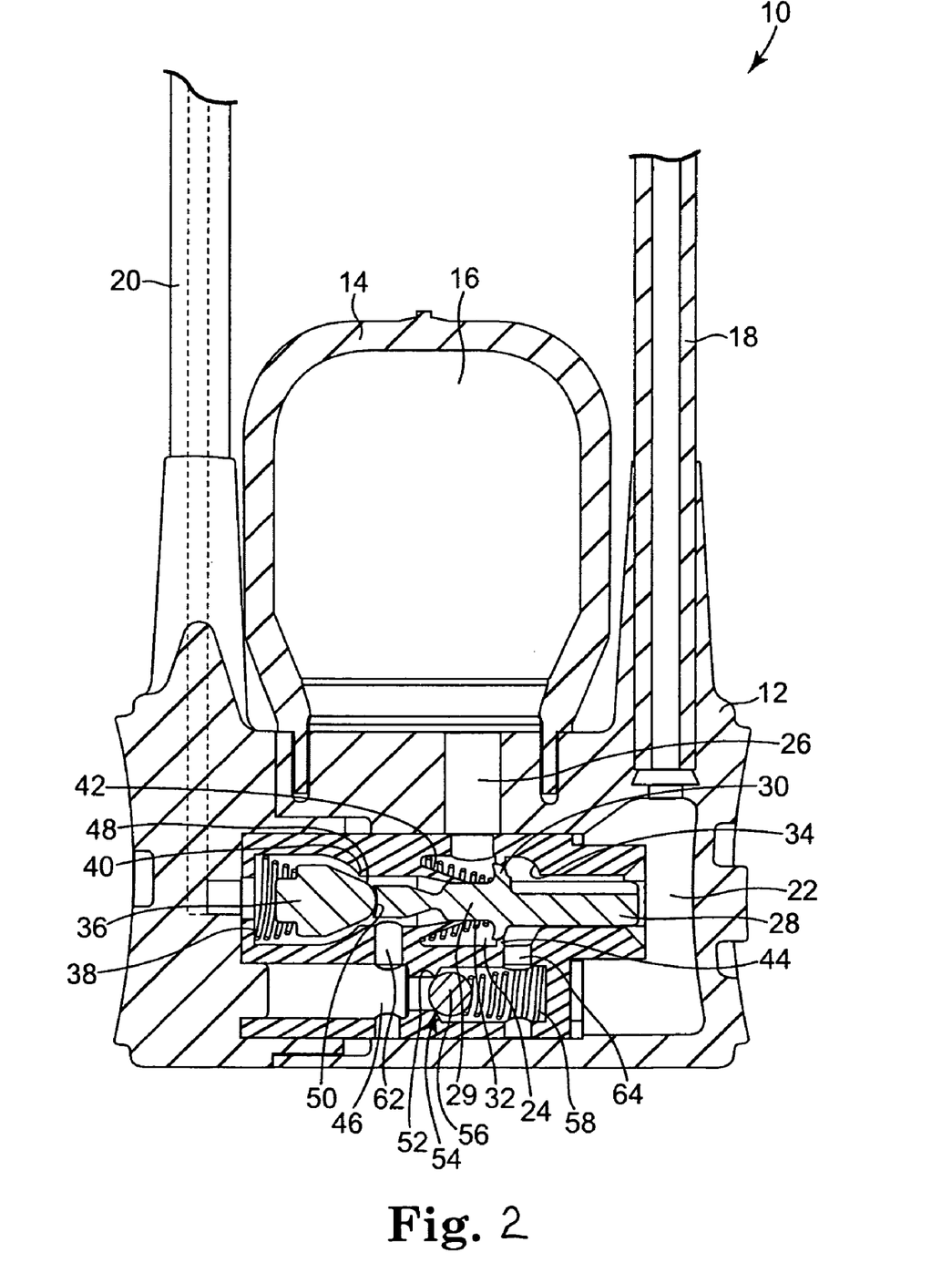
FIG. 2 is a partial cross-sectional front view of one embodiment of a pump assembly of an implantable penile prosthesis device of the present invention, with the pump configured in its auto-inflation resistance mode.

One preferred configuration of a pump assembly 10 for use in an implantable penile prosthesis system, such as device 110, is illustrated in FIG. 2. In general, when the penile prosthesis system is implanted into a person, the pump assembly 10 is positioned within the user's scrotum, two inflatable cylinders are positioned within the user's corpus cavernosae and a reservoir is implanted in the user's abdomen. One or more tubes provide fluid communication between the assembly 10 and the cylinders and between the assembly 10 and the reservoir. In this embodiment, the assembly 10 includes a housing or pump body 12 connected to a pump bulb 14 having an internal pump chamber 16. The pump assembly 10 is connected for fluid communication with at least one inflatable cylinder (not shown) by at least one tube 18, which may be a flexible silicone tube, for example. While only one such tube 18 is visible in FIG. 1, the assembly 10 may include additional tubes 18 for connection to multiple inflatable cylinders. Alternatively, a single tube 18 could be fluidly connected directly to the pump assembly 10 and branch into multiple tubes that extend to each of the cylinders at some distance from the pump assembly. Each tube 18 is preferably relatively flexible for comfort and conformability within a patient, and may have a constant or varying (e.g., tapered) diameter along its length.

The pump assembly 10 is further connected for fluid communication with at least one fluid-filled reservoir (not shown) by at least one reservoir tube 20. While only one tube 20 is visible in FIG. 1, the assembly 10 may include additional tubes 20 for connection to one or more reservoirs, or a single tube 20 may be fluidly connected to the pump assembly and branch into multiple tubes that connect to one or more reservoirs. In the preferred embodiment, however, a single tube 20 is provided to fluidly connect the pump assembly 10 to a single reservoir, which is typically implanted in the abdomen or some other location in the user's body that is spaced from the pump assembly 10. Each tube 20 is preferably made of a relatively flexible material, such as silicone, and is sufficiently long for connecting the reservoir to the pump body when these components are implanted in their desired locations in the body.

The pump assembly 10 of the present invention is controllable by the user to move fluid to and from the inflatable cylinders, as desired. Importantly, the pump assembly 10 is designed to eliminate or reduce the possibility of the cylinders becoming deflated unintentionally. In addition, when the reservoir is at least partially inflated, the pump assembly 10 preferably maintains fluid pressure in the reservoir to maintain it in its inflated or semi-inflated state until the user desires to inflate the cylinders. Thus, the pump assembly 10 provides a controllable device that is easily manipulated by the user to inflate and deflate the cylinders, as desired.

The pump body 12 is preferably a generally flexible device that includes a number of components to provide the desired movement of fluid through its internal chambers. More specifically, one end of the reservoir tube 20 is fluidly connected to a transfer chamber 22 within the pump body 12. Transfer chamber 22 can also fluidly communicate with one end of transfer tube 18 through a connecting fluid passageway 24. The fluid passageway 24 is further connected to the internal pump chamber 16 of pump bulb 14 by a connecting channel 26, where the various fluidic connections can be initiated and terminated with the operation of the pump assembly 10, as described below. As shown, fluid passageway 24 is a generally elongated chamber that extends across a portion of the width of the pump body 12 and provides a passageway through which fluid can flow between the components of the pump assembly 10, such as the reservoir, pump bulb 14, a fluid bypass chamber 46, and the cylinders.

Fluid passageway 24 includes within its internal area a check valve system that generally includes a suction poppet 28 and a poppet 36. Suction poppet 28 and poppet 36 are preferably aligned with each other along the length of the passageway 24, with both poppets preferably being centrally positioned within the passageway 24. The suction poppet 28 has a generally elongated shape including several contours for contact and sealing with various components of the system during its operation. In particular, suction poppet 28 includes an elongated body 29 that is preferably generally cylindrical, although it can take any number of shapes that fit within the internal chamber of the fluid passageway 24 to provide contact with its surfaces and control the movement of fluid. The suction poppet 28 further includes a face seal portion 30 that is preferably a ring-like protrusion that extends around the outer perimeter of the elongated body 29. As shown, the face seal portion 30 is positioned near the center of the length of the elongated body 29, although it is possible that the portion 30 is closer to one of the ends of the elongated body 29 than its other end. The face seal portion 30 is shaped to abut a suction poppet valve seat 34, which is a contoured surface formed within the passageway 24. The surface of the valve seat 34 that comes into contact with the face seal portion 30 is preferably a generally smooth surface that allows for a fluid tight seal between the face seal portion 30 and valve seat 34, when desired. Suction poppet 28 further includes a suction poppet spring 32 that engages suction poppet 28 and biases suction poppet 28 toward the valve seat 34, or toward the right side of the pump body 12 in this Figure.

Fluid passageway 24 further includes a flange 44 configured generally as a ring-like portion within the passageway 24 that preferably extends toward the center of the passageway 24 around the inner perimeter of the fluid passageway 24. The flange 44 is provided to reduce the inner diameter of the passageway 24 by a sufficient amount that the inner diameter in the area of the flange 44 is smaller than the outer diameter of the face seal portion 30. In this way, the flange 44 can engage with the face seal portion 30 to hold the suction poppet 28 against the bias of the spring 32. The flange 44 preferably has sufficient strength to hold the face seal portion 30 against the bias of the spring 32, but also is flexible enough to allow movement of the face seal portion 30 through or past the flange 44 in either direction (i.e., to the right or left). The flange 44 may be annular and extend around the inner perimeter of the passageway 24, as shown, or may instead have a different shape or configuration that can provide the function of engaging and disengaging sufficiently with the face seal portion 30 in the manner described above. Further, the flange 44 may formed integrally with the passageway 24 or may be formed separately and attached to the interior of the passageway 24, such as with adhesives or the like. Suction poppet spring 32 is preferably has sufficient spring force to provide the desired amount of sealing between the face seal portion 30 and the valve seat 34 when the face seal portion 30 is to the right of the flange 44. The spring 32 should not be so strong, however, that it pushes the suction poppet 28 past the flange 44 toward the transfer chamber 22 when it is instead desired for the face seal portion 30 to be on the opposite side of flange 44.

Fluid passageway 24 also includes within its internal area a poppet valve seat 40 adjacent to the poppet 36. Poppet valve seat 40 is an inner surface area that is shaped to allow only a portion of the poppet 36 to extend past it. That is, the poppet 36 is preferably provided with a generally tapered outer surface that allows it to partially move past or through the poppet valve seat 40 until the outer surface of the poppet 36 contacts the valve seat 40. Thus, as the poppet 36 moves to the right in the figure, the outer surface of the poppet 36 will come into contact with the poppet valve seat 40, thereby providing a fluid tight seal in certain modes of the operation of the pump assembly 10. Poppet 36 is provided with a poppet spring 38 that engages poppet 36 and biases poppet 36 toward poppet valve seat 40. The poppet spring 38 is preferably strong enough to provide a fluid tight seal between the poppet 36 and the poppet valve seat 40; however, the spring 38 is preferably not so strong that the poppet 36 is prevented from being moved to the left under sufficient fluid pressure. Such a movement of the poppet 36 away from the poppet valve seat 40 allows fluid to pass from the fluid passageway 24 into the tube 20 during operation of the pump assembly 10.

The internal area or portion of the fluid passageway 24 further includes a lip seal 42 that extends generally from the area near the poppet 36 toward the suction poppet 28. In one preferred embodiment, the lip seal 42 may be generally conical in shape such that it tapers from a first cross-section in the pump body to a point or edge at its other end. This lip seal 42 is shown in cross-section as a finger-like portion that extends into the fluid passageway 24. It is contemplated, however, that the lip seal 42 has a different configuration or shape for sealing against the surface of the suction poppet 28. Lip seal 42 is preferably configured so that it can contact the outer walls of the suction poppet 28 and provide a fluid tight seal between the lip seal 42 and the suction poppet 28 when the suction poppet is positioned as shown in FIG. 2 (i.e., with the face seal portion 30 out of contact with the valve seat 34 and to the left of the flange 44). Lip seal 42 is preferably further configured to allow smooth movement of the suction poppet 28 into and out of contact with the lip seal 42. However, lip seal 42 will be spaced from the outer walls of the suction poppet 28 when the portion of the suction poppet 28 that is adjacent to the lip seal 42 is smaller in diameter than the area adjacent the lip seal 42. This will occur, for example, when the suction poppet 28 is moved so that the face seal portion 30 is in contact with the valve seat 34, as described below. In this mode, fluid would then be able to move through the fluid passageway 24 and past the lip seal 42.

As illustrated in FIG. 2, the poppet 36 includes a nose portion 48 that is contoured to engage with an end 50 of suction poppet 28. In this way, when the suction poppet 28 is moved away from the valve seat 34 so that the face seal portion 30 is engaged with the flange 44 against the bias of the suction poppet spring 32, the end 50 of suction poppet 28 will push against the nose 48 of the poppet 36 against the bias of poppet spring 38, thereby allowing for a certain fluid flow path. Thus, it is also preferable that the poppet spring 38 and the suction poppet spring 32 are chosen to provide the desired ease of movement of components. That is, undue force should not be required to move the springs and poppets through the various operation modes of the pump assembly 10. In particular, it is required for operation of the pump assembly 10 that the sides of the pump body 12 are compressible to thereby manipulate the position of suction poppet 28 and poppet 36 relative to each other and the pump body 12. In order for this to be possible, it is preferable that suction poppet 28 and poppet 36 are in sufficiently close proximity to the sides of the pump body 12 so that squeezing the pump body 12 with a reasonable amount of force will move the components within the pump body 12 into certain positions.

Pump body 12 further includes a fluid bypass chamber 46 that is connected for fluid communication with the fluid passageway 24 under certain operating conditions or modes of the pump. Fluid bypass chamber 46 includes a ball check valve 54 having a ball 56 and a spring 58. The spring 58 biases the ball 56 within the chamber 46 toward a ball valve seat 52, which is a portion or edges of the chamber 46 that form a diameter that is smaller than the diameter of the ball 56. In this way, a fluid tight seal may be formed between the ball 56 and the ball valve seat 52 when the system is in a state of equilibrium. This seal prevents the undesired movement of fluid through the bypass chamber 46 except under certain operating conditions of the pump assembly 10. As with the other springs used in pump assembly 10, spring 58 should be sufficiently strong to keep the ball 56 in its normal or closed position against the ball valve seat 52 under many operating circumstances. However, the spring 58 should also allow for a predetermined flow of fluid against the bias of the spring 58 to move the ball 56 out of contact with the ball valve seat 52 to allow fluid to flow through the bypass chamber 46. As shown, fluid may move from the fluid passageway 24 into the bypass chamber 46 through a bypass input channel 62, which is positioned to the left of the lip seal 42.

When there is a sufficient volume of pressurized fluid in the chamber 46 to move the ball 56 against the bias of the spring 58, the fluid will be able to move freely from the input channel 62 and through the bypass chamber 46. Fluid may then exit the bypass chamber 46 through a bypass output channel 64 that provides a second fluid connection between the bypass chamber 46 and the fluid passageway 24. The bypass output channel 64 is positioned to the right of the lip seal 42 so that certain operating conditions will provide a fluid path in which fluid passes by the suction poppet 28 and enters the transfer chamber 22. The valve style used in the fluid bypass chamber 52 of FIG. 1 is shown as a ball check valve, but it could instead include any number of designs such as a "duck bill valve", flap, or the like, which react to pressurized fluid in generally the same manner as the ball check valve 54.

FIG. 2 illustrates the pump assembly 10 with its components in a configuration that may be referred to as an auto-deflation resistance mode. In this mode, the cylinders are in an inflated condition and spontaneous deflation of the cylinders will preferably be difficult or impossible due to the positions of the poppets, springs and chambers of the pump assembly 10. No deflation of the cylinders can occur until the pump bulb 14 is manipulated in a specified manner. In this mode, the fluid of the system will typically be contained within tube 18 and the connected transfer chamber 22, and this fluid cannot travel into the reservoir tube 20 and the attached reservoir. In this mode, the suction poppet 28 is being held against the bias of the suction poppet spring 32 by the flange 44 within the fluid passageway 24. The end 50 of suction poppet 28 is engaged with the nose portion 48 of poppet 36, thereby pushing the poppet 36 against the bias of poppet spring 38. The suction poppet 28 is thus positioned so that its outer surface is in contact with the lip seal 42, thereby creating a fluid-tight seal between the suction poppet 28 and the lip seal 42.

In most cases, some portion of the fluid from the cylinders will move into the tube 18 and transfer chamber 22, particularly when the cylinders are under pressure. Any such pressurized fluid in the transfer chamber 22 can move into the fluid passageway 24 and move the suction poppet 28 slightly to the left. This movement of suction poppet 28 allows fluid to flow from the transfer chamber 22 through the gap between the face seal portion 30 and suction poppet valve seat 34. This fluid will then enter the internal pump chamber 16 through the connecting channel 26. Movement of fluid into the pump bulb 14 will stop when the pressure has generally equalized between the pump bulb 14 and the cylinders. The bias of suction poppet spring 32 can then move the face seal portion 30 back into contact with the valve seat 34, thereby limiting or preventing further fluid flow into the pump bulb 14.

Because the lip seal 42 and suction poppet 28 form a fluid tight seal, as described above, no fluid may move past this seal toward the tube 20 and connected reservoir. In addition, fluid moving into the fluid bypass chamber 46 through the bypass output channel 64 will be prevented from moving past the ball check valve 54 by the seal of the ball 56 against the ball valve seat 52. Thus, no fluid will be able to pass into the fluid passageway 24 or the tube 20 by this path. In this state of equilibrium, fluid will thus be held within the cylinders, the connecting tube 18, the transfer chamber 22, and the internal pump chamber 16. While there may be small amounts of residual fluid contained in the various portions of the pump assembly, it is understood that the reservoir is preferably in its completely deflated or collapsed condition when the pump is configured in this mode.

Figure 3:
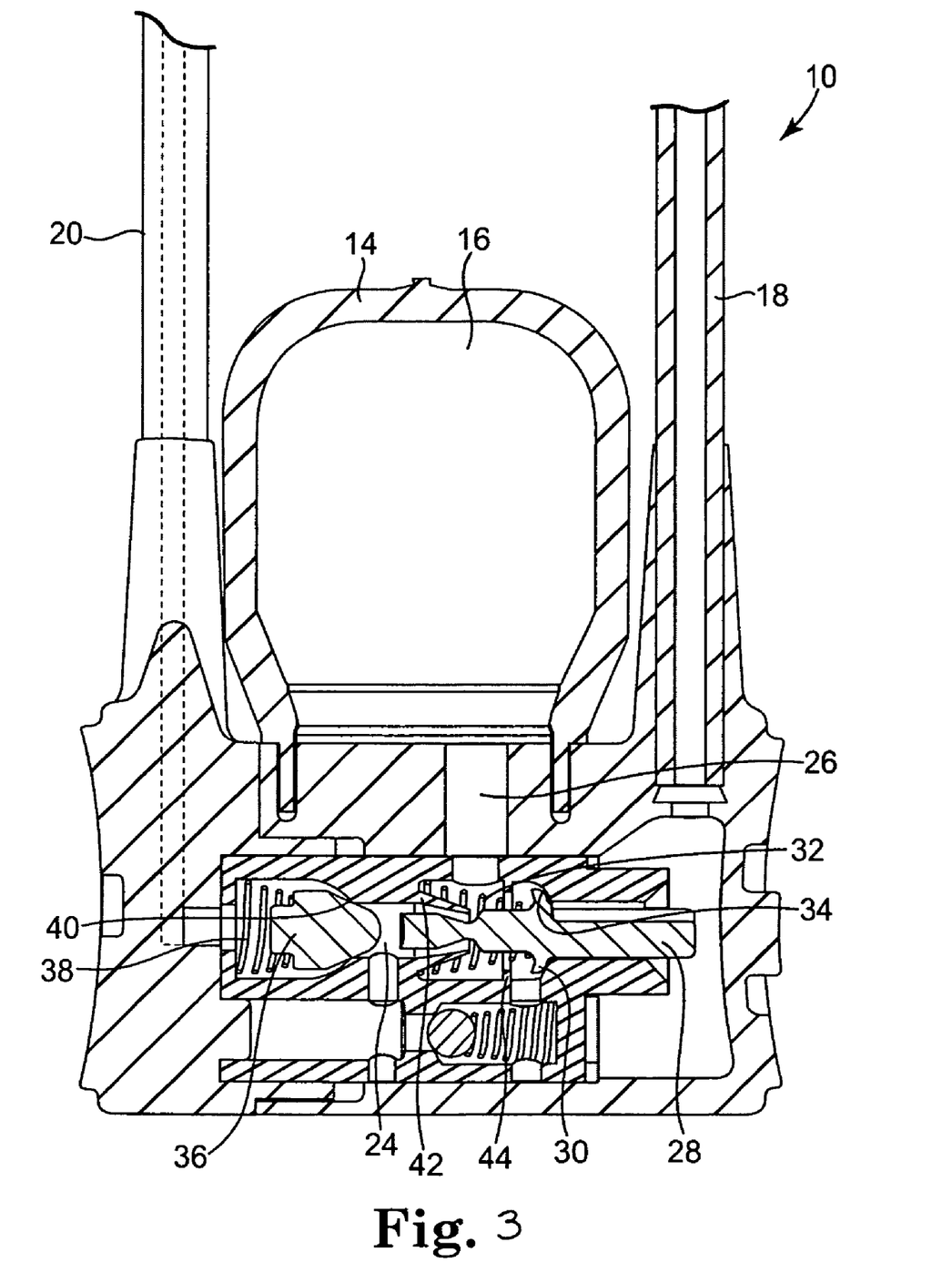
FIG. 3 is a partial cross-sectional front view of a pump assembly of the type illustrated in FIG. 1, with the pump configured in its activation mode.

The activation mode of pump assembly 10 for cylinder deflation is illustrated in FIG. 3. This is the mode in which the user activates the pump assembly to begin the process of cylinder deflation. To activate the pump assembly 10, the pump bulb 14 is squeezed or compressed by the user. This motion forces the fluid contained within pump chamber 16 through connecting channel 26 and into fluid passageway 24 under relatively high fluid pressure. This high pressure fluid forces the face seal portion 30 of suction poppet 28 past the flange 44, which is made of a material that is relatively flexible to allow the face seal portion 30 to move past it, yet sufficiently strong to hold the suction poppet 28 against the bias of its spring 32. The bias of the suction poppet spring 32 will then push the suction poppet 28 and its face seal portion 30 against the suction poppet valve seat 34, thereby providing a fluid tight seal between the face seal 30 and the valve seat 34. Because the portion of the suction poppet 28 adjacent the lip seal 42 is now smaller in diameter than the internal opening provided by the lip seal 42, the lip seal 42 is not in contact with the suction poppet 28 in this mode (i.e., a gap is created between the suction poppet 28 and the lip seal 42). Thus, fluid can move past lip seal 42 and toward the poppet 36. In order for fluid to move past the poppet 36 and into the tube 20, however, the fluid pressure must be high enough to overcome the bias of the poppet spring 38, which is now pushing the poppet 36 in fluid tight contact with the poppet valve seat 40. The amount and pressure of the fluid may or may not be sufficient to cause such a movement of poppet 36 in this pump activation mode.

Figure 4:
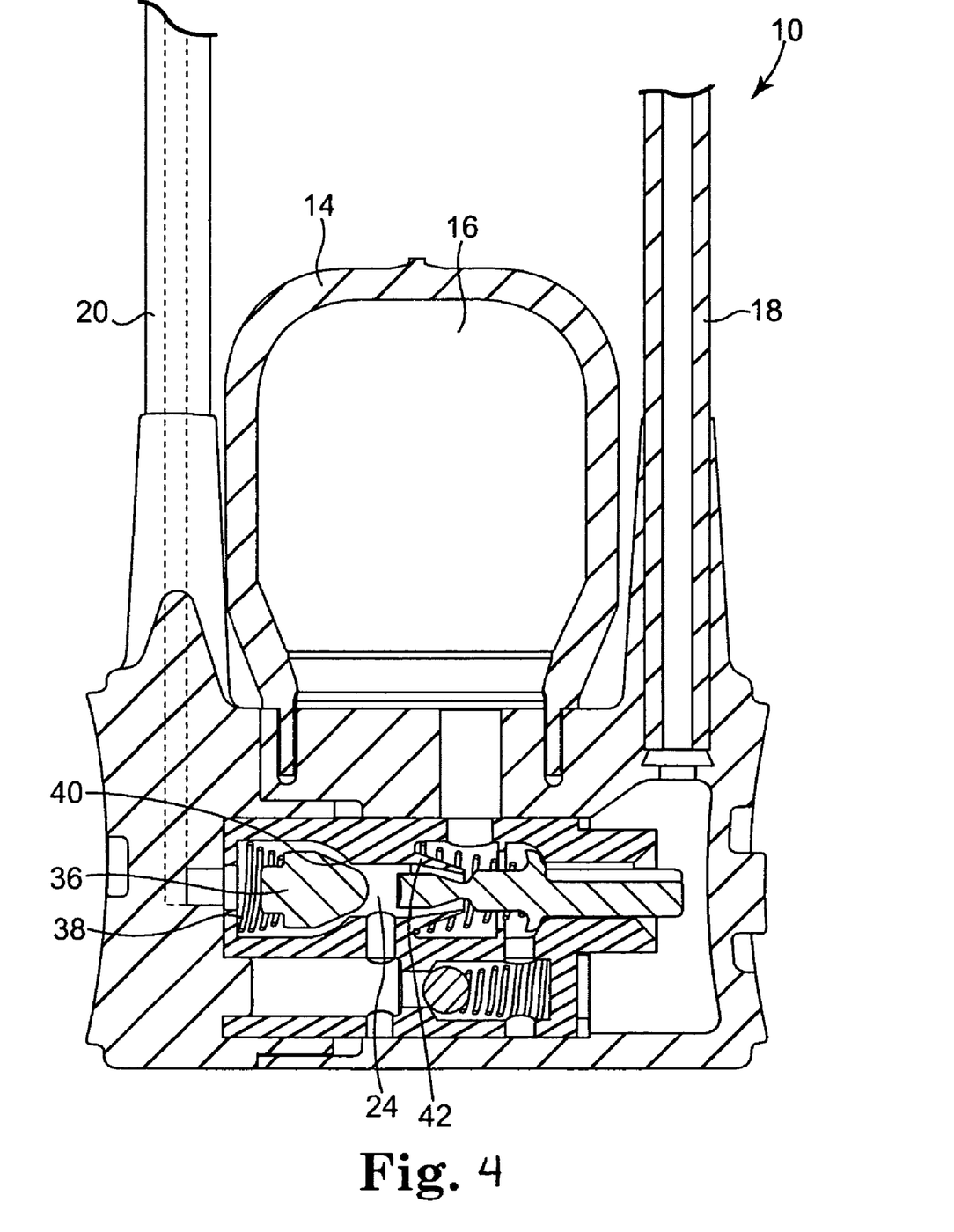
FIG. 4 is a partial cross-sectional front view of a pump assembly of the type illustrated in FIG. 1, with the pump configured in its pumping mode.

FIG. 4 illustrates a situation where the fluid pressure is sufficiently high to overcome the bias of the poppet spring 38, thereby breaking the fluid-tight contact between the poppet 36 and poppet valve seat 40 and providing a gap between these two surfaces. This may be referred to as the pumping mode of pump assembly 10. Fluid may then flow past the lip seal 42 and poppet 36, and then into the tube 20 and the attached reservoir. In particular, after a first volume of pressurized fluid from the pump bulb is moved past the poppet 36 and into the reservoir (e.g., as described above relative to FIG. 3), the bias of the poppet spring 38 will push the poppet 36 back into contact with the poppet valve seat 40. Pump bulb 14 is preferably selected from a material that is relatively elastic and easy for a user to compress, but should also have sufficient structural integrity that it tends to move back toward its original size or configuration when not subjected to external pressure. That is, when the user releases the bulb 14, it should expand generally to its original shape and size, thereby providing a situation where the pump bulb chamber 16 and fluid passageway 24 are placed under negative pressure. This negative pressure provided by the expansion of the bulb 14 will draw fluid from the cylinders through the tube 18 and into the pump bulb 14, as illustrated in FIG. 5.

Figure 5:
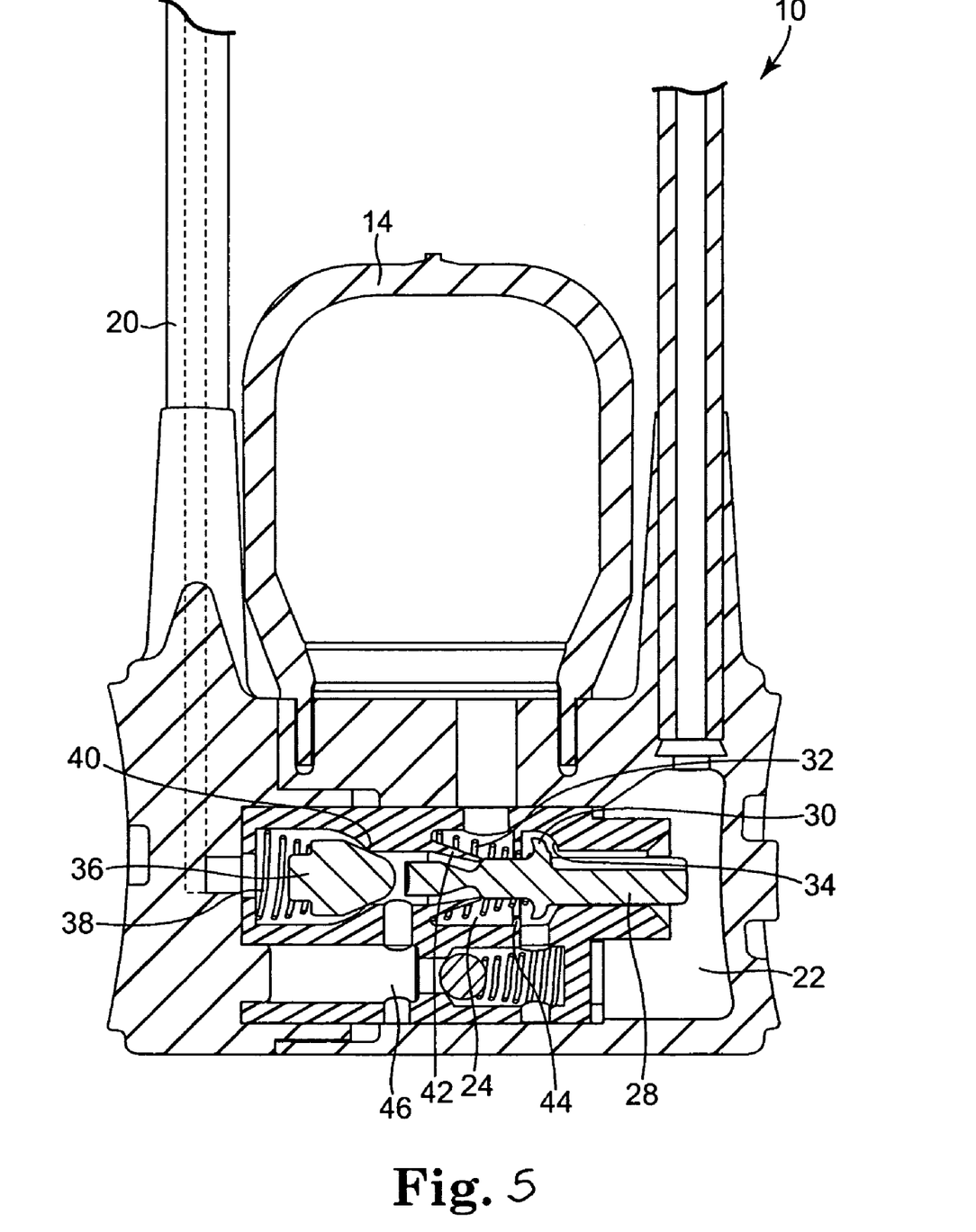
FIG. 5 is a partial cross-sectional front view of a pump assembly of the type illustrated in FIG. 1, with the pump configured in its pump bulb filling mode.

More specifically, FIG. 5 shows the pump assembly 10 in the mode that may be referred to as the pump bulb filling mode. As described above, this mode exemplifies the situation in which the pump bulb 14 is pulling or drawing fluid from the cylinders and through the various chambers of the system. As shown, the negative pressure within the pump bulb 14 and connected chambers moves the suction poppet 28 slightly to the left, thereby breaking the seal between the face seal portion 30 and the suction poppet valve seat 34. Simultaneously, the outer portion of the suction poppet 28 will slide into contact with the lip seal 42 to provide a fluid tight seal between the suction poppet 28 and lip seal 42. Fluid may then flow from the cylinders into the transfer chamber 22, past the face seal portion 30, and into the fluid passageway 24. Because the lip seal 42 and suction poppet 28 are positioned to provide a fluid tight seal, no fluid may move past these surfaces. Rather, any fluid under negative pressure within the fluid passageway 24 will move into the pump bulb 14 until the pump bulb 14 is full and/or there is no longer enough fluid pressure to keep the face seal portion 30 from moving toward the suction poppet valve seat 34. The suction poppet spring 32 then causes the suction poppet 28 to reseat itself against the valve seat 34. At this point, the user may then squeeze or compress the pump bulb 14 to again move fluid from the pump bulb 14 into the tube 20 and attached reservoir, as described above relative to FIG. 4.

This sequence of filling the pump bulb 14 under negative pressure and forcing the fluid from the pump bulb 14 under positive pressure may be repeated as many times as necessary to achieve the desired deflation of the cylinders and/or to fill or partially fill the connected reservoir. Once inflated, the fluid within the reservoir and the tube 20 is under relatively high pressure. While the poppet spring 38 preferably has a sufficiently strong bias to keep the poppet 36 pressed against the poppet valve seat 40, the relatively high pressure fluid in the reservoir and connected chambers also pushes the poppet 36 into contact with the valve seat 40, further strengthening this seal. This seal between the poppet 36 and valve seat 40 is particularly important to keep the cylinders deflated (i.e., to prevent undesirable transfer of fluid from the reservoir into the fluid passageway 24). Because the only path for fluid to move from the tube 20 into the fluid bypass chamber 46 is through the fluid passageway 24, it is likewise not possible for fluid from the reservoir to move into the fluid bypass chamber 46 without first breaking the seal between the poppet 36 and its poppet valve seat 40.

Figure 6:
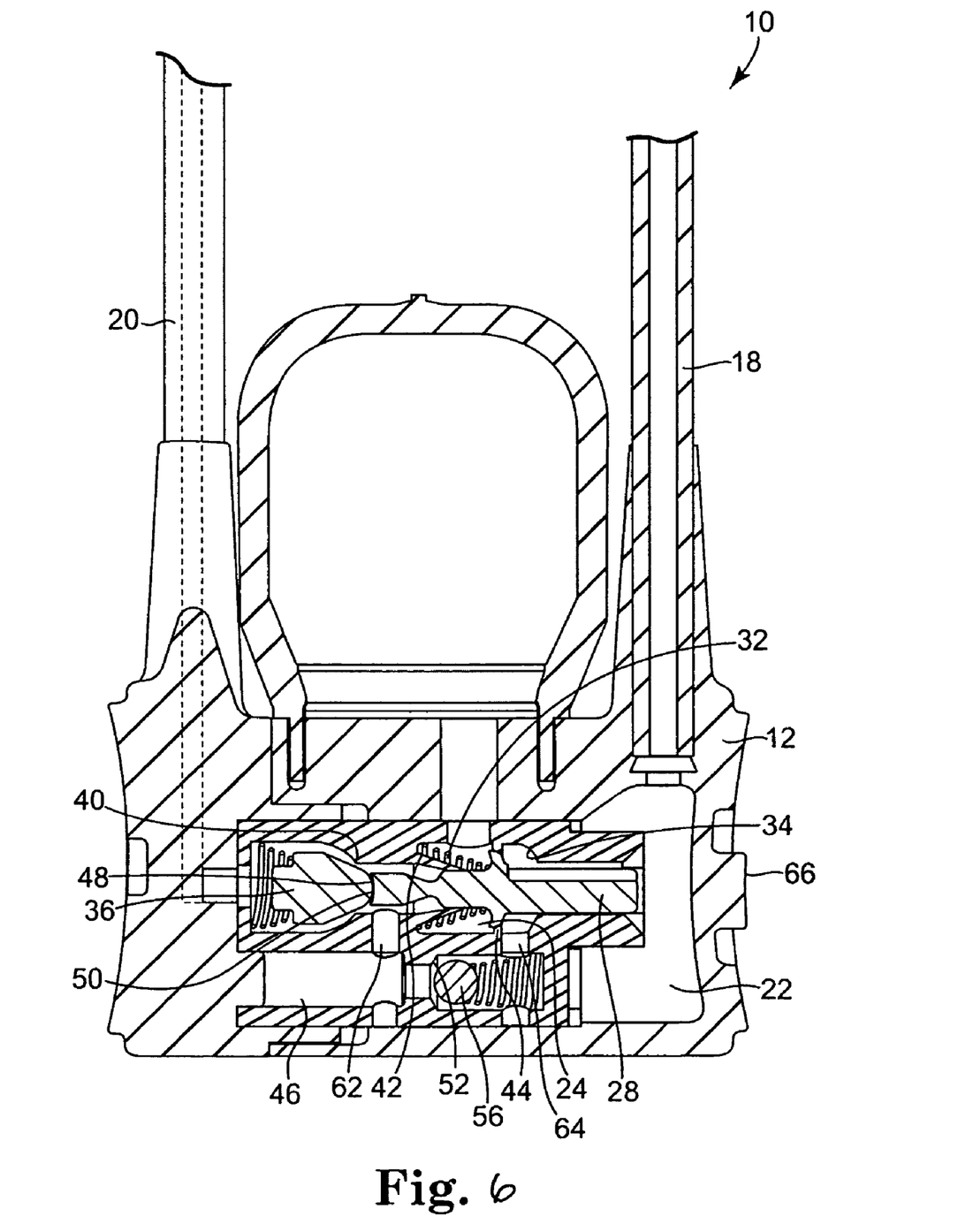
FIG. 6 is a partial cross-sectional front view of a pump assembly of the type illustrated in FIG. 1, with the pump configured in its inflation mode where inflation of the cylinders occurs.

When the user desires to inflate the cylinders, the walls of the pump body 12 will be manually compressed in the general area of the fluid passageway 24, as shown in FIG. 6. In order to assist the user in finding the proper area for compression, the outer surface of the pump body 12 may be provided with raised or otherwise detectable areas for easier determination of proper manipulation locations on the pump body 12. One example of such a detectable area is illustrated as a user pressure pad 66, which is a raised flat area on the side of the pump body 12 that would be detectable by the human fingers. A compressive force on both ends of the pump body 12 forces suction poppet 28 away from the suction poppet valve seat 34 by a sufficient distance that the face seal portion 30 moves to the left past the flange 44. The flange 44 then engages the face seal portion to hold the suction poppet 28 in place against the bias of the suction poppet spring 32. This compression of the pump body 12 simultaneously moves the end 50 of suction poppet 28 into contact with the nose portion 48 of poppet 36, which also breaks the seal between the poppet 36 and the poppet valve seat 40. Further, the pump body compression also causes the suction poppet 28 to be in a position where the lip seal 42 is in contact with the suction poppet 28, which provides a fluid tight seal between these surfaces. Fluid from the reservoir and connecting tube 20 may then flow around the poppet 36, past the poppet valve seat 40, and into the bypass input channel 62. Notably, a single compressive squeeze by the user is sufficient to put the pump assembly 10 in this cylinder inflation mode, which can advantageously allow for quick inflation of the cylinders with minimal user manipulation. In other words, there is no need for the user to continue to hold the pump body 12 in this compressive condition while the cylinder inflation is occurring. Once the fluid enters the bypass input channel 62, it moves directly into the fluid bypass chamber 46, where sufficient fluid pressure can unseat the ball 56 from the ball valve seat 52 and allow fluid to move out of the chamber 46 through the bypass output channel 64 and into the fluid passageway 24. The fluid can then move through the transfer chamber 22 to the tube 18, and then into the cylinders.

Because the fluid within the reservoir before deflation is under relatively high pressure, an initial volume of pressurized fluid will move under pressure from the tube 20 and into the pump body 12 upon compression of the pump body. In order to deflate the reservoir and inflate the cylinders, the valve body of the pump is squeezed to open the valves within the pump, as described above, which allows pressurized fluid from the reservoir to move through the pump and fully inflate the cylinders. No further manipulation of the device is required to achieve this completely full state of the cylinders. Deflation of the cylinders can be accomplished by squeezing the pump bulb of the pump repeatedly. Because the pressure within the reservoir is preferably relatively constant, the force that is required for each squeeze of the bulb should also be relatively constant. Further, because the cylinders of this system are pressurized before deflation, the pump bulb should refill rapidly after each release of the bulb. In this embodiment, the cylinders preferably include an expanding fabric, but may instead include a non-expanding fabric, if desired.

Figure 7:
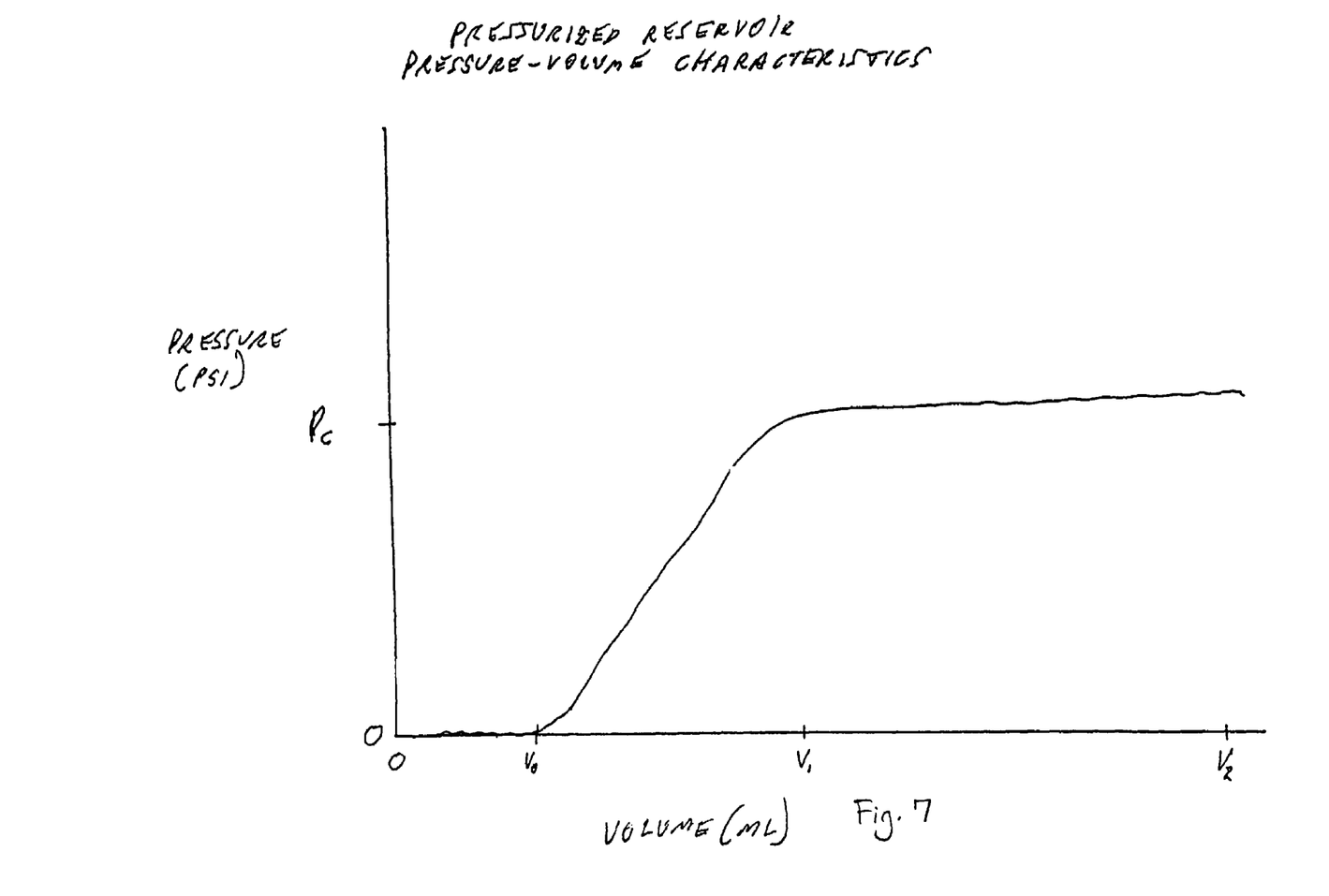
FIG. 7 is a graph of the pressure-volume characteristics of a prosthesis device in accordance with the present invention.

As described above and illustrated graphically in FIG. 7, the reservoir is preferably made of a thick-walled material so that the reservoir can maintain a relatively constant pressure after an initial volume of fluid expands the reservoir, even if more fluid is added to the reservoir after the initial filling. Thus, when the reservoir is filled from a volume $V_1$ to a volume $V_2$, the pressure inside the reservoir remains at a pressure $P_c$. Similarly, as the volume in the reservoir is reduced from $V_2$ to $V_1$, the pressure remains relatively constant at $P_c$. This pressurized reservoir facilitates quicker inflation of the cylinders when the valve body is squeezed because the squeezing of the valve opens all of the pump valves and puts the reservoir in direct fluid communication with the cylinders. Fluid can move from the reservoir to the flaccid and empty cylinders due to the pressure differential between the reservoir and the cylinders, and the fluid flow will continue until the cylinders expand and the pressure in the reservoir and cylinders are in equilibrium at $P_c$. As long as the volume required to fully inflate the cylinders is equal to or less than the difference between $V_1$ and $V_2$, the cylinder pressure will be $P_c$. If the volume required to fully inflate the cylinders is greater than the difference between $V_1$ and $V_2$, (such as when larger cylinders are used) the equilibrium pressure will decrease to some value along the curve between $V_1$ and $V_0$. In this case, adding more fluid beyond the volume $V_2$ can accommodate the additional fluid requirement. If the cylinders are smaller, however, the reservoir can be filled to a volume that is less than $V_2$.

Although the description above is directed to a particular pump configuration, the invention includes within its scope other pumps having a valve assembly that allows for relatively quick inflation of cylinders with minimal pump manipulation, even if the deflation of those cylinders requires more substantial manipulation of the pump. Another example of such a pump is that shown in U.S. Pat. No. 6,730,017 (Henkel et al.), commonly owned by the assignee of the present invention. In particular, the prior art described therein includes a valve assembly having a configuration similar to that described above relative to FIGS. 2-6, but without a bypass valve.

The reservoir and cylinders are preferably made of a relatively flexible membrane that is sized to hold a sufficient amount of fluid for proper inflation and deflation, when desired. In particular, the reservoir membrane is preferably relatively elastic so that the membrane can stretch to hold all of the fluid transferred from the cylinders and can collapse when the fluid is transferred from the reservoir to the cylinders. However, the reservoir membrane does not necessarily need to be elastic. The membrane should also be strong enough to hold fluid under pressure within the reservoir for extended periods of time without the membrane relaxing or otherwise deteriorating and losing pressure.

In accordance with the present invention, when the cylinders are filled or partially filled with fluid, the cylinder membranes will be stretched in such a way that the fluid within the cylinders is under pressure and the cylinders act as an energy-storage device or capacitor. To activate the device and inflate the reservoir, the user activates the pump by squeezing the pump bulb, which causes the fluid in the pump bulb to move through a pump body and enter the reservoir. The fluid will continue to move from the cylinders and into the reservoir until the fluid from the pump bulb is transferred from its internal chamber. At this point, the reservoir will be partially filled. The user may then repeatedly squeeze the pump bulb to transfer more fluid from cylinders to the reservoir until the cylinders reach a desired flaccidity. Thus, the system of the present invention acts as an energy transfer system, where the particular valves, passageways, and chambers can be chosen from a wide variety of configurations and components, with the cylinders and reservoir alternately acting as the energy storage component of the system.

The systems of the present invention can utilize any inflatable and implantable cylinders that inflate and collapse as generally described for the pump and reservoir systems of this invention. Thus, the cylinders may be shaped and connected to the tubing generally as shown in the FIGS., but may instead have a different shape or contours, and may attach to the tubing in a different manner than that shown. However, in one preferred embodiment of the present invention, the cylinders are of a type having a non-expanding fabric. Preferably, the cylinders comprise parylene coated silicone inner and outer tubes. The cylinders may alternatively be of a type that includes an expanding fabric, if desired. Further, it is preferable that the entire device be adapted to include an antimicrobial treatment by providing a fluid-filling port, valve, or septum, so that it can be filled in the operating room.

It is understood that the number of tubes and the branching of tubes can differ from that specifically described herein, depending on the design of the pump and other components. As described above relative to the pump assembly 10, the body of the pump assembly can be squeezed generally along its longitudinal axis in order to inflate the cylinders, which thereby opens certain valves within the pump and allows pressurized fluid from the reservoir to move through the pump and enter the cylinders. Deflation of the cylinders can be accomplished by first squeezing the pump bulb to activate the pump assembly, then squeezing the pump bulb repeatedly until the desired cylinder deflation is achieved. Further, while the use of a pressurized fluid in the embodiments of the present invention describe several exemplary embodiments, it is understood that the concepts of pressurizing fluid in these types of systems is adaptable to systems with various types of pumps, cylinders, and reservoirs that provide the same features as those described relative to the present invention.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A penile prosthesis comprising:
    at least one cylinder;
    a reservoir; and
    a pump for transferring fluid between the reservoir and the at least one cylinder, the pump comprising:
    a pump housing;
    at least one reservoir channel fluidly coupling the pump housing to the reservoir;
    at least one cylinder tube fluidly connecting the pump housing to the at least one cylinder;
    a fluid passageway fluidly coupled to the reservoir channel and a transfer chamber and comprising a flange extending toward its interior, wherein the transfer chamber is fluidly coupled to the at least one cylinder tube;
    a first poppet biased toward a first valve seat within the fluid passageway and comprising an elongated body having an extending face seal portion for engagement with the flange of the fluid passageway when the first poppet is displaced by a sufficient distance from the first valve seat;
    a second poppet biased toward a second valve seat, biased away from the first valve seat, and generally in alignment with the first poppet within the fluid passageway, wherein the fluid passageway further comprises a lip seal portion that extends generally from the second poppet toward the first poppet;
    a bypass chamber fluidly connected by a bypass input channel to the fluid passageway at a first location that is located on a side of the lip seal adjacent the second poppet and fluidly connected by a bypass output channel to the fluid passageway at a second location that is located on a side of the lip seal that is further from the second poppet than the bypass input channel, the bypass chamber comprising a bypass check valve biased toward a closed position; and
    a pump bulb fluidly connected to the fluid passageway between the bypass input channel and bypass output channel along the length of the fluid passageway;
    wherein the pump has a inflation mode in which compression of a portion of the pump body moves the first poppet into sealing contact with both the lip seal portion and the second poppet to unseat the second poppet from the second valve seat to provide a gap between the second poppet and the second valve seat for pressurized fluid to flow from the reservoir past the second poppet and into the bypass chamber through the bypass input channel.

2. The prosthesis of claim 1, further comprising a cylinder deflation mode in which the face seal portion of the first poppet is seated against the first valve seat, the lip seal portion is spaced from the first poppet, and the pump bulb is compressible for forcing enough fluid under pressure from the pump bulb into the fluid passageway to unseat the second poppet from the second valve seat and allow fluid to move past the second poppet and enter the reservoir.

3. The prosthesis of claim 1, wherein the reservoir is expandable in response to movement of pressurized fluid from the at least one cylinder through the pump and into the reservoir, thereby pressurizing the fluid within the reservoir.

4. The prosthesis of claim 1, wherein a fluid pressure level of fluid flowing from the reservoir into the bypass chamber is sufficient to unseat the ball from the ball valve seat and allow fluid to flow through the bypass output channel and into the transfer chamber of the pump housing.

5. The prosthesis of claim 1, wherein the at least one cylinder tube is an opening extending from the transfer chamber through the pump housing for fluidly connecting the transfer chamber to the at least one cylinder.

6. The prosthesis of claim 1, wherein the reservoir comprises an outer reservoir membrane surrounding at least a portion of an internal reservoir chamber, wherein the reservoir chamber can expand from a first internal volume to a second internal volume that is larger than the first internal volume by the addition of pressurized fluid.

7. The prosthesis of claim 1 wherein the bypass check valve comprises a ball biased toward a ball valve seat within the bypass chamber.

8. The prosthesis of claim 1, further comprising a filling port fluidly connected to the transfer chamber for adding a predetermined volume of fluid to the prosthesis.

9. A pump for transferring fluid between a reservoir and at least one cylinder within a penile prosthesis, the pump comprising:
    a pump housing;
    at least one reservoir channel for fluidly coupling the pump housing to a reservoir;
    at least one cylinder tube for fluidly connecting the pump housing to at least one cylinder;

a fluid passageway fluidly coupled to the at least one cylinder tube and a transfer chamber and comprising a flange extending toward its interior, wherein the transfer chamber is fluidly coupled to the at least one cylinder tube;

a first poppet biased toward a first valve seat within the fluid passageway and comprising an elongated body having an extending face seal portion for engagement with the flange of the fluid passageway when the first poppet is displaced by a sufficient distance from the first valve seat;

a second poppet biased toward a second valve seat, biased away from the first valve seat, and generally in alignment with the first poppet within the fluid passageway, wherein the fluid passageway further comprises a lip seal portion that extends generally from the second poppet toward the first poppet;

a bypass chamber fluidly connected by a bypass input channel to the fluid passageway at a first location that is located on a side of the lip seal adjacent the second poppet and fluidly connected by a bypass output channel to the fluid passageway at a second location that is located on a side of the lip seal that is further from the second poppet than the bypass input channel, the bypass chamber comprising a bypass check valve biased toward a closed position; and a pump bulb fluidly connected to the fluid passageway between the bypass input channel and bypass output channel along the length of the fluid passageway, wherein the pump bulb is repeatedly compressible for deflation of the at least one cylinder.

* * * * *